United States Patent [19]

Fields

[11] 4,358,597
[45] Nov. 9, 1982

[54] THIOCARBAMATES OF 1,3,4-THIADIAZOLE-2,5-DITHIOL

[75] Inventor: Ellis K. Fields, River Forest, Ill.

[73] Assignee: Standard Oil Company (Indiana), Chicago, Ill.

[21] Appl. No.: 725,011

[22] Filed: Sep. 20, 1976

[51] Int. Cl.$^3$ .................. C07D 285/12; A01N 47/18; A01N 47/20
[52] U.S. Cl. .................................. 548/142; 546/108; 546/143; 546/162; 546/277; 252/51.5 A; 252/356; 252/391; 424/270
[58] Field of Search ................ 260/302 SD; 548/142; 546/108, 143, 162, 277

[56] References Cited

U.S. PATENT DOCUMENTS 2,685,588 8/1954 Goshorn et al. ............. 260/302 SD
3,980,573 9/1976 Okorodudv ..................... 252/46.7

Primary Examiner—Alton D. Rollins
Attorney, Agent, or Firm—William C. Clarke; William T. McClain; William H. Magidson

[57] ABSTRACT

A thiocarbamate compound selected from the group of thiocarbamate compounds consisting of 1,3,4-thiadiazole-2-thiol-5- monothiocarbamate; 1,3,4-thiadiazole-2,5-dithiocarbamate; 1,3,4-thiadiazole-2-thiol-5-mono(dithiocarbamate) and 1,3,4-thiadiazole-2,5-di(dithiocarbamate). These thiocarbamate compounds can be represented by the general formula

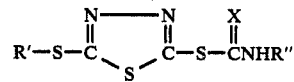

where R' is a monovalent radical individually selected from the group consisting of a hydrogen radical and the radical

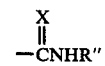

wherein X is selected from the group consisting of =O and =S, and R" is selected from the group consisting of hydrogen moieties, alkyl moieties containing 1 to 22 carbon atoms, and aralkyl moieties, alkylated aryl moieties, heterocyclic alkyl moieties, cycloalkyl moieties containing 6 to 40 carbon atoms joined to the

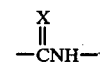

group, the said moieties being unsubstituted and substituted, said substitutions being individually selected from the group consisting of halogen moieties, nitro moieties, alkoxy moieties, alkyl moieties, and carboalkoxy moieties.

6 Claims, No Drawings

THIOCARBAMATES OF 1,3,4-THIADIAZOLE-2,5-DITHIOL

BACKGROUND OF THE INVENTION

The field of this invention relates to novel compositions of matter which are thiol-esters of 1,3,4-thiadiazole-2,5-dithiol. These compounds are prepared by selective cyanation of 1,3,4-thiadiazole-2,5-dithiol. These novel compounds are surface active agents suitable for surfactants, have rust inhibiting properties and biocidal activity as fungicides for agricultural use.

Organic sulfur compounds are of considerable industrial importance. Novel organic sulfur compounds with characteristics suitable for use in soluble oil compositions, tertiary oil recovery micellar fluids and miscellaneous uses such as pesticides are of extensive utility. For example, steam turbine and other industrial oils can be stabilized against the rusting of ferrous parts should water become mixed with the oil. An important use of soluble oils is as lubricating and cooling agents in the cold working of metals such as in grinding, cutting and threading operations. For this use, the soluble oil is dispersed in from about 10 to 80 or more times its own volume of water and circulated over the contact point of the working tool and the metal being worked on. Frequently, difficulty is encountered in this type of operation due to the tendency of the soluble oil emulsion or dispersion to cause rusting of metals in contact with such emulsions, particularly ferrous metals and also because in the course of time, these emulsions or dispersions develop strong, putrid, undesirable odors if the soluble oil composition does not contain a bactericide.

The use of fungicides in agricultural applications is also of considerable agricultural significance. Fungicides are used at low rates as seed protectants and disinfectants on a major portion of total crop acreages. Since fungi often develop tolerance to fungicides after a period of exposure, an availability of new fungicides is constantly needed for continuing control.

DESCRIPTION OF THE PRIOR ART

This invention relates to thiocarbamates of 1,3,4-thiadiazole-2,5-dithiol as new compositions of matter and their use as surface active agents, rust inhibitors and fungicides.

The preparation of thiocarbamates and dithiocarbamates, forms of thiol-esters, is well-known as among the most characteristic reactions of the isocyanates and isothiocyanates are those reactions with compounds containing "active" hydrogens. Accordingly, isocyanates and isothiocyanates react typically with compounds containing labile hydrogen at a sulfur-hydrogen bond. (N. K. Kharasch, *Organic Sulfur Compounds, I.*, Pergamon, New York, 332 (1961)) (Kirk-Othmer, Ency. Chem. Tech., 10, 399 (1953)). Thiocarbamates and dithiocarbamates can result in the presence of Friedel-Crafts catalysts, tertiary amines, cobalt naphthenate, dibutyl tin maleate, diphenyl tin chloride and antimony pentachloride with a mixture of an isocyanate or isothiocyanate and a mercaptan. (C. H. Rodd, *Chem. of Carbon Cpds, III*, Elsevier, N.Y., 194 (1954)). Application of heat to approximately 100° C. can be necessary for the reaction in the case of sterically hindered isocyanates or isothiocyanates.

SUMMARY OF THE INVENTION

Novel thiocarbamates and dithiocarbamates are prepared by selective cyanation of 1,3,4-thiadiazole-2,5-dithiol which can be substituted with carbon moieties of up to 40 carbon atoms which, in turn, can be substituted with halogen, nitro, alkoxy and carboalkoxy groups. These compounds are prepared by reacting thiadiazoles with isocyanates or isothiocyanates in a liquid phase reaction, preferably under ambient conditions or at about $-20°$ to $100°$ C. They are useful as surfactants, rust inhibitors and fungicides.

DETAILED DESCRIPTION OF INVENTION

Novel thiocarbamate thiol-ester compounds selected from the group consisting of 1,3,4-thiadiazole-2-thiol-5-monothiocarbamate; 1,3,4-thiadiazole-2,5-dithiocarbamate; 1,3,4-thiadiazole-2-thiol-5-mono(dithiocarbamate) and 1,3,4-thiadiazole-2,5-di(dithiocarbamate) are prepared by selective cyanation of 1,3,4-thiadiazole-2,5-dithiol in the presence of a catalyst. These novel compositions of matter can be represented by the general formula

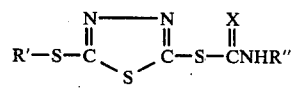

where R' is a monovalent radical individually selected from the group consisting of a hydrogen radical and the radical

where =X is individually selected from the group consisting of =O and =S and R" is selected from the group consisting of hydrogen moieties, alkyl moieties containing 1 to 22 carbon atoms, and aralkyl moieties, alkylated aryl moieties, heterocyclic alkyl moieties, cycloalkyl moieties containing 6 to 40 carbon atoms wherein the said moieties are joined to the carbonyl or thiocarbonyl group through the alkyl chain, the said moieties being unsubstituted and substituted, said substitutions being individually selected from the group consisting of halogen moieties, nitro moieties, alkoxy moieties, alkyl moieties, and carboalkoxy moieties.

The thiocarbamates of this invention have the following structures, namely:

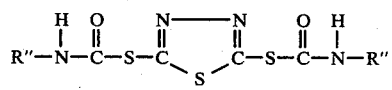

(1) a bis 2,5-thiocarbamate,

(2), a bis-2,5-dithiocarbamate,

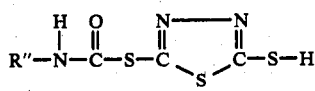

(3), a 2-thiocarbamate,

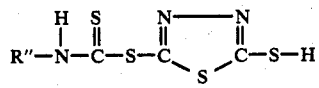

and (4), a 2-dithiocarbamate, wherein R″ is defined as given above.

Typical compounds of this invention include:
2,5-bis(N-methylcarbamylthio)-1,3,4-thiadiazole
2,5-bis(N-phenylcarbamylthio)-1,3,4-thiadiazole
2,5-bis(N-ethylcarbamylthio)-1,3,4-thiadiazole
2,5-bis(N-isopropylcarbamylthio)-1,3,4-thiadiazole
2,5-bis(N-methylthiocarbamylthio)-1,3,4-thiadiazole
2,5-bis(N-phenylthiocarbamylthio)-1,3,4-thiadiazole
2-(N-propylcarbamylthio)-1,3,4-thiadiazole-5-thiol The novel thiocarbamate compounds derived from 1,3,4-thiadiazole-2,5-dithiol, commonly named 2,5-dimercaptothiadiazole or DMTD, which are the subject of my invention, can be summarized as being of a family of thiocarbamates of DMTD, the particular thiocarbamate of the group of thiol esters being dependent upon whether the reactant with DMTD is a isocyanate or an isothiocyanate. If an isocyanate is used, the result is a 2,5-dimonothiocarbamate. If an isothiocyanate is used, the result is a 2,5-dithiocarbamate.

For purposes of this invention the term "thiocarbamates" is defined as including monothiocarbamates, dithiocarbamates, mono(dithiocarbamates) and di(dithiocarbamates). The term "thiocarbamates" is further defined as indicating a type of thiol-ester which is the reaction product of a thiol (or mercaptan) and an isocyanate or an isothiocyanate in cyanation reaction analogous to an esterification reaction between an acid and an alcohol. The term "cyanation" is defined as indicating a reaction wherein a reactive hydrogen is replaced by a cyano or thiocyano group. The term "bis" is defined, as in the Condensed Chemical Dictionary, 9th Ed., Reinhold, 1971, as indicating a chemical grouping or radical occurs twice in a molecule, or as in Hackh's Chemical Dictionary, "bis" indicates twice and is generally applied to molecules made up of two similar halves. The term "alkyl moiety" is defined as including monovalent chain saturated hydrocarbon groups containing 1 to 22 carbon atoms, i.e., methyl, ethyl, propyl, isopropyl, butyl and isobutyl, 2-ethylhexyl, amyl, hexyl, heptyl, dodecyl, octyl, isotridecyl, stearyl and tetracosyl groups. The term "aralkyl moiety" is defined as including groups composed of monovalent chain saturated hydrocarbon moieties containing from 1 to 22 carbon atoms attached to aromatic moieties containing 6 to 18 carbon atoms such as phenyl, biphenyl, naphthyl, anthranyl, etc. Typical examples of these moieties, but not limited to these examples, are benzyl, β-phenylethyl, 3-phenylpropyl, 4-phenylbutyl, etc. The term "alkylated aryl moieties" is defined as including aromatic moieties containing 6 to 18 carbon atoms, i.e., phenyl, biphenyl, naphthyl, anthranyl, etc., the said aromatic moieties such as benzene or naphthalene being substituted with alkyl groups up to ten in number, the said alkyl groups containing from one to four carbon atoms as well as dimers, trimers, etc., of alkyl groups, i.e., propylene or isobutylene dimers, trimers, tetramers up to quatradecamers. Typical examples, but not limited to these examples, are t-octylphenyl isocyanate, t-dodecylisocyanate, t-octadecyl isocyanate, the dimer, trimer and tetramers of these compounds, as well as nonylphenyl isocyanates, and pentadecyl isocyanates. The term "heterocyclic alkyl moieties" is defined as a group containing a cyclic or ring structure of five or more atoms in the ring in which one or more atoms in the ring is an element other than carbon and can be oxygen, nitrogen and/or sulfur, the ring structure attached to an alkyl group containing 1 to 22 carbon atoms, the said ring structure containing up to three cyclic analogues. Examples are thienyl, pyridyl, benzothienyl, thienobenzenyl, quinolyl, isoquinolyl, dibenzothienyl and phenanthridyl groups. The term "cycloalkyl moieties" is defined as including saturated cyclic moieties such as the monocyclic groups cyclohexyl, cycloheptyl, cyclooctyl, the dicyclic groups and the tricyclic groups such as decahydronaphthalene (decalin), perhydroanthracene and perhydrophenanthrene containing up to 40 carbon atoms. The above same groups can be substituted or unsubstituted, containing such substituents such as halogens (fluorine, chlorine, bromine and iodine), nitro and alkyl groups, alkoxy groups such as methoxy, ethoxy, propoxy, butoxy, decyloxy and dodecyloxy groups.

In general, the reaction of the DMTD is carried out with the isocyanate or isothiocyanate by reacting 2 to 3 moles of the cyanate reactant with one mole of DMTD in an aprotic solvent such as ether, tetrahydrofuran, benzene, diethyl ether, carbon tetrachloride, diisopropyl ether, dioxane or 1,2-dimethoxyethane at a temperature within the range from −20° C. to 100° C. for a period up to 240 hours depending on reaction rate. A basic catalyst such as a trialkylamine in concentrations of 0.001 to 2% can be added. A trialkylamine catalyst is preferred because it need not be recovered. Preferred ratio is 2 moles of isocyanate or isothiocyanate to 1 mole of DMTD as DMTD has two reactive sites. Preferred catalyst concentration is 0.01 to 1%. Preferred catalyst is triethylamine or tributylamine. Preferred solvent is anhydrous ether.

In general, the R″ group of the isocyanate or isothiocyanate R″NCO and R″NCS can be a straight or branched chain alkyl group containing 1 to 22 carbon atoms, preferably 1 to 4 carbons for fungicidal use, preferably 4 to 18 carbon atoms for soluble oil use; an aralkyl group, an alkylated aryl group, a heterocyclic alkyl group, a cyclo alkyl group, the last four containing 6 to 40 carbon atoms for longlasting herbicidal use, preferably 6 to 24 carbon atoms, and the same groups containing substituents such as halogen, nitro, alkoxy or carboalkoxy groups. Examples of these R″ groups are n-butyl, n-hexyl, isobutyl, n-dodecyl, isostearyl, benzyl, p-methylbenzyl, β-phenethyl, naphthyl, 4-chloro-i-butyl, β-nitrobutyl, 3-methoxy-butyl, 1-diethylaminoethyl, 4-nitrobenzyl, 4-chlorobenzyl, 4-diethylaminobenzyl, 2-chloromethyl furyl, methyl thienyl, pyridyl, cyclohexyl, 4-fluoro-1-cyclohexyl, 2-methoxy cyclopentyl, 6-nitroquinolyl, and 6-diethylamino-2-isoquinolyl.

In general, in the preparation of the instant compounds, the reaction is carried out by adding an isocyanate or isothiocyanate to the thiadiazole-dithiol (which is DMTD) or vice-versa, and maintaining the mixture at a temperature of from about −20° C. to about 100° C. for a period of from about 10 minutes to about 240 hours. Since the reaction can be exothermic, cooling by liquid circulation can be necessary. Maximum reaction temperature with adequate cooling is about 100° C. because speed of reaction can be excessive over 100° C. or decomposition can occur. Preferred reaction temperature is 10° to 30° C. Below 10° C., the reaction rate is very slow. Heat can be necessary for hindered isocyanates such as 2,6-dimethyl isocyanate or 2,4,6-trimethyl isocyanate. Above 100° C., the thiocarbamates can decompose to the original DMTD and isocyanate or isothiocyanate. Preferably, the reaction is carried out in the presence of a suitable solvent, such as by way of example, dioxane, diethyl ether ethylene glycol dimethyl and diethyl ethers, and diethylene glycol dimethyl and diethyl ethers. At the end of the reaction, the solvent is removed from the reaction product, preferably by stripping in a vacuum, and the stripped product filtered if necessary. A monothiocarbamate or monodithiocarbamate can be recovered from the mother liquor.

Although the herein described thiadiazole derivatives all exhibit to a definite degree anti-rust properties, surfactant properties, and pesticide control properties, all are not necessarily equivalent in their effectiveness, since, depending upon the nature and severity of the service in which they are used, some variation in effectiveness may be exhibited. These compounds can be used as surfactants if they contain long chain groups or t-alkyl groups, or alkylated aromatics such as would result from p-t-hexadecylphenylisocyanate. Surfactants can also be obtained with alkylated polymers where R″ can be benzene or naphthalene containing alkyl substituents of 1 to 200 carbon atoms such as obtained by alkylating benzene or naphthalene with propylene or isobutylene dimers, trimers, tetramers up to quatradecamers.

In summary, the invention consists of a family of thiocarbamates which are prepared by the reaction of isocyanates and isothiocyanates with 1,3,4-thiadiazole-2,5-dithiol (DMTD) wherein the alkyl moiety of said isocyanates and isothiocyanates is selected from the group consisting of methyl, ethyl, propyl, isopropyl, butyl, isobutyl, 2-ethylhexyl, amyl, hexyl, heptyl, dodecyl, octyl, isotridecyl, stearyl, tetracosyl moieties, the said aryl or heterocyclic moiety being selected from the group consisting of phenyl, biphenyl, naphthyl, anthranyl, thienyl, pyridyl, benzothienyl, thienobenzenyl, quinolyl, isoquinolyl, dibenzothienyl, phenanthridyl, cyclohexyl, cycloheptyl, cyclooctyl, decahydronaphthalene, perhydroanthracene, perhydrophenanthrene moieties, said moieties when substituted, being substituted with substituents selected from the group of substituents consisting of fluorine, chlorine, bromine, iodine, nitro, methoxy, ethoxy, propoxy, butoxy, decyloxy and dodecyloxy substituents.

The preparation of the above-described reaction products is illustrated by the following examples, which are given by way of illustration and are not intended to limit the scope of the invention.

The following examples illustrate the preparation of thiocarbamates using isocyanates and DMTD.

EXAMPLE I

A solution of 7.5 g (0.05 mole) of 1,3,4- thiadiazole-2,5-dithiol (DMTD) was stirred in 700 ml of anhydrous ether in a 3-necked round-bottom flask equipped with a thermometer, a reflux condenser, a dropping funnel, and a magnetic stirrer. The solution was maintained at below 25° C. by cooling while 5.9 ml (0.1 mole) of methyl isocyanate and 0.2 ml of triethylamine were added dropwise. The reaction mixture was stirred at 25° C. for 48 hours. The yellow-solid crystals were collected on a filter, washed with ether and dried. The product was 8.2 grams (62 mole % yield) m.p. 162° C., 2,5-bis(N-methylcarbamylthio)-1,3,4-thiadiazole.

Analysis: Calcd. for $C_6H_8N_4S_3O_2$: N, 21.2%, S, 36.3%. Found: N, 20.9%, S, 36.4%.

EXAMPLE II

In the procedure of Example I, to a solution of 3.75 g. (0.025 mole) of 1,3,4-thiadiazole-2,5-dithiol and 5.044 ml. (0.05 mole) of phenyl isocyanate in 350 ml. of anhydrous ether was added 0.2 ml. of triethylamine. Heat was evolved and the solid product came out of solution. After 24 hours at 25° C. the product was collected on a filter, washed with ether, and dried: 5.5 g. (57% yield), m.p. 166°–167°. Product was 2,5-bis(N-phenylcarbamylthio)-1,3,4-thiadiazole.

Analysis: Calcd. for $C_6H_{12}N_4O_2S_3$: C, 49.5; H, 3.1; N, 14.4; S, 24.7 Found: C, 49.3; H, 3.2; N, 14.5; S, 24.2

EXAMPLE III

The procedure of Example I was repeated. A solution of 7.5 g. (0.05 mole) of 1,3,4-thiadiazole-2,5-dithiol, 7.84 ml. (0.1 mole) of ethyl isocyanate, and 0.2 ml. of triethylamine in 700 ml. of anhydrous ether was kept at 25° C. for 10 days. The clear solution was concentrated to 150 ml. and cooled at 0° C., giving 6.1 g. product melting at 157° (dec.). The mother liquor gave another 8.0 g. of product upon being evaporated. Total yield of crude product, 96%. The product was 2,5-bis(N-ethylcarbamylthio)1,3,4-thiadiazole.

Analysis: Calcd. for $C_8H_{12}N_4O_2S_3$: C, 32.9; H, 4.1; N, 19.2; S, 32.9 Found: C, 32.0; H, 3.5; N, 20.0; S, 33.4

EXAMPLE IV

In the procedure of Example I, a solution of 7.5 g. (0.05 mole) of 1,3,4-thiadiazole-2,5-dithiol, 8.51 g. (0.1 mole) of n-propylisocyanate, and 0.2 ml. of triethylamine was kept at 25° C. for 10 days. The clear solution was concentrated to 75 ml. and cooled at 0° C. to give 7 g. (44%) of product A,. m.p. 108°–109° C. The filtrate, on being evaporated, gave 9.1 of product B (77%), m.p. 124°, soluble in aqueous potassium carbonate. Product A was 2,5-bis(N-propylcarbamylthio)-1,3,4-thiadiazole.

Analysis: Product A. Calcd for $C_{10}H_{16}N_4O_2S_3$: C, 31.3; H, 5.0; N, 17.5; S, 30.0 Found: C, 31.4; H, 5.0; N, 18.0; S, 30.4

Product B was 2-(N-propylcarbamylthio)-1,3,4-thiadiazole-5-thiol.

Analysis: Product B. Calcd. for $C_6H_9N_3OS_3$: C, 30.6; H, 3.8; N, 17.8; S, 40.8 Found: C, 30.9; H, 3.9; N, 18.1; S, 40.2

EXAMPLE V

A solution of 7.5 g. (0.05 mole) of 1,3,4-thiadiazole-2,5-dithiol, 8.51 g. (0.1 mole) of isopropyl isocyanate, and 0.2 ml. of triethylamine in 700 ml. of anhydrous ether was kept at 25° C. for 10 days. The ether was evaporated, the residue was dissolved in 50 ml. of benzene, and cooled to 10° C. The crystalline solid was collected on a filter, washed with 10 ml. of cold benzene, and air-dried. The solid, 9.6 g. (60% yield) melted at 146° C. (dec.). Product was 2,5-bis(N-isopropylcarbamylthio)-1,3,4-thiadiazole.

Analysis: Calcd. for $C_{10}H_{16}N_4O_2S_3$: C, 31.3; H, 5.0; N, 17.5; S, 30.1 Found: C, 31.4; H, 4.6; N, 18.4; S, 30.6

The compounds of my invention were tested as fungicides against diseases of significant agricultural crops with these results:

Compound of Example I against R. Solani as a soil fungicide

| Parts per million (ppm) | % Control |
|---|---|
| 250 | 100 |
| 100 | 92 |
| 50 | 83 |
| 25 | 75 |

For comparison, Captan, a commercial soil fungicide, gave 100%, 100%, and 50% control at 100, 50 and 25 parts per million.

Compound of Example II was tested against late blight of tomatoes

| ppm | % Control |
|---|---|
| 1000 | 99 |
| 500 | 93 |
| 250 | 86 |
| 100 | 58 |

At 1000 ppm, it gave 88% control of leaf rust of wheat and 82% control of bacterial leaf spot of tomatoes.

Compound of Example III was tested. At 1000 ppm it gave 84% control of late blight of tomatoes, 100% control of leaf rust of wheat, and 82% control of bacterial leaf spot of tomatoes. As a soil fungicide at 50 lbs./acre it gave 38% control of stem rot of peanuts, 80% and 60% control against damping off, and 40% control against verticillium wilt. It also had some activity as a post-emergence herbicide.

Compound of Example IVA was tested. At 1000 ppm it gave 83% control of late blight of tomatoes, 87% against leaf rust of wheat, and 81% against bacterial leaf spot of tomatoes. At 50 lbs./acre it gave 92% control of damping off and showed some herbicidal activity.

Compound of Example IVB was tested. At 1000 ppm it gave 83% control of late blight of tomatoes, 93% of leaf rust of wheat, and 80% of bacterial leaf spot of tomatoes. At 50 lbs./acre it gave 35% control of stem rot of peanuts, and 46% control of damping off.

Compound of Example V was tested. At 1000 ppm it gave 74% control of late blight of tomatoes, 91% of leaf rust of wheat, and 82% of bacterial leaf spot of tomatoes. At 50 lbs./acre it gave 80% and 40% control of damping off, 56% control of bean root rot, and 45% control of verticillium wilt. It also had some herbicidal activity.

The following examples illustrate the preparation of dithiocarbamates using isothiocyanates and DMTD.

EXAMPLE VI

To a solution of 7.5 g. (0.05 mole) of 1,3,4-thiadiazole-2,5-dithiol in 700 ml. of anhydrous ether were added 6.84 ml. (0.1 mole) of methyl isothiocyanate, then 0.2 g. of triethylamine. The solution was stored at 25° for 10 days, then evaporated on the steam bath. The product, 14.6 g. (98 mole % yield) was a thick viscous yellow oil. Product was 2,5-bis(N-methylthiocarbamylthio)-1,3,4-thiadiazole.

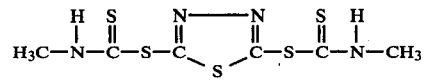

Anal. calcd. for $C_6H_8N_9S_5$: N, 18.9%; S, 54.1% Found: N, 18.3%; S, 54.3%.

EXAMPLE VII

To a solution of 7.5 g. (0.05 mole) of 1,3,4-thiadiazole-2,5-dithiol in 700 ml. anhydrous ether were added 11.87 ml. (0.1 mole) of phenylisothiocyanate, then 0.2 g. of triethylamine. The solution was stored at 25° for 10 days, then evaporated on a steam bath to give 17.3 g. (93 mole % yield) of a yellow-solid that melted at 148°–149° with decomposition after crystallization from benzene. Product was bis-2,5-(N-phenylthiocarbamylthio)-1,3,4-thiadiazole.

Analysis calcd. for $C_{16}H_{12}N_4S_5$: N, 13.3%; S, 38.3% Found: N, 13.1; S, 38.2%

The compound of Example VI induced 100% control of Leaf Rust of Wheat at 1000 ppm, and 100% control of root knot nematode at 50 lb./A. There was no indication of phytotoxicity in either test. The compound of Example VII induced 61% control of R. Solani at 50 lb./A.

What I claim is:

1. A thiocarbamate compound of the general formula

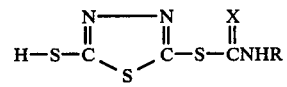

wherein X is selected from the group consisting of =O and =S and R is selected from the group consisting of hydrogen moieties, alkyl moieties containing 1 to 22 carbon atoms, and aralkyl moieties, alkylated aryl moieties, heterocyclic alkyl moieties, cycloalkyl moieties containing 6 to 40 carbon atoms joined to the

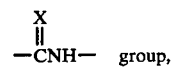 group, the said moieties being unsubstituted and substituted, said substitutions being individually selected from the group consisting of halogen moieties, nitro moieties, alkoxy moieties, alkyl moieties and carboalkoxy moieties.

2. A thiocarbamate compound of the general formula

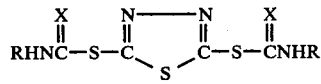

wherein X is selected from the group consisting of =O and =S, and R is selected from the group consisting of hydrogen moieties, alkyl moieties containing 1 to 22 carbon atoms, and aralkyl moieties, alkylated aryl moieties, heterocyclic alkyl moieties, cycloalkyl moieties containing 6 to 40 carbon atoms joined to the

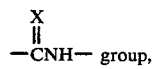
—CNH— group, the said moieties being unsubstituted and substituted, said substitutions being individually selected from the group consisting of halogen moieties, nitro moieties, alkoxy moieties, alkyl moieties and carboalkoxy moieties.

3. The thiocarbamate compound of claim 1 which comprises 2-(N-propylcarbamylthio)-1,3,4-thiadiazole-5-thiol.

4. The thiocarbamate compound of claim 2 which comprises 2,5-bis (N-methylcarbamylthio)-1,3,4-thiadiazole.

5. The thiocarbamate compound of claim 2 which comprises 2,5-bis (N-ethylcarbamylthio)-1,3,4-thiadiazole.

6. The thiocarbamate compound of claim 2 which comprises 2,5-bis (N-isopropylcarbamylthio)-1,3,4-thiadiazole.

* * * * *